United States Patent [19]
Michaeli

[11] Patent Number: 5,840,018
[45] Date of Patent: Nov. 24, 1998

[54] NON-INVASIVE REAL TIME DIAGNOSIS OF MIGRAINE

[75] Inventor: David Michaeli, Ashkelon, Israel

[73] Assignee: INTA Medics Ltd., Israel

[21] Appl. No.: 864,579

[22] Filed: May 28, 1997

[51] Int. Cl.⁶ .................................. A61B 5/00; A61B 8/06
[52] U.S. Cl. .............................................. 600/300; 600/449
[58] Field of Search ................................ 600/407, 419, 600/437, 449, 451, 454, 504–507

[56] References Cited

U.S. PATENT DOCUMENTS

| | | | |
|---|---|---|---|
| 4,008,711 | 2/1977 | Olingar et al. | 600/586 X |
| 4,928,705 | 5/1990 | Seklar et al. | 600/586 |
| 5,187,672 | 2/1993 | Chance et al. | 600/407 X |
| 5,357,959 | 10/1994 | Fishman | 600/420 |
| 5,388,583 | 2/1995 | Ragaushas et al. | 600/451 |

*Primary Examiner*—Francis Jaworski
*Attorney, Agent, or Firm*—Jones & Askew

[57] ABSTRACT

A method of real-time determination of variations in effective diameter of cranial blood vessels, thereby to provide an indication of migraine activity, which includes determining the blood flow rate to the brain of a subject; determining the intracranial blood flow rate in selected blood vessels; and comparing the intracranial blood flow rate with the determined blood flow rate to the brain thereby to determine a change in the intracranial blood flow rate relative to the blood flow rate to the brain, indicating a corresponding change in the effective diameter of the preselected blood vessel.

18 Claims, 11 Drawing Sheets

NON-INVASIVE REAL TIME DIAGNOSIS OF MIGRAINE

FIELD OF THE INVENTION

The present invention relates generally to diagnosis and study of migraine by observation of variations in the blood flow in the brain.

BACKGROUND OF THE INVENTION

It is known that many people suffer from headaches, and a significant portion suffer from migraine. A significant portion of migraine sufferers do not turn to neurology departments of medical institutions, but rather turn to their family doctor for prescription on an ad hoc basis.

Migraine is known to be diagnosed via clinical examinations and non-objective means. One objective finding known to be closely associated with migraine is variation, contraction or dilation, of blood vessels in the brain. In order to measure this, in many cases, patients are sent for MRI or CT examinations—examinations that are very costly and that often involve a long waiting time. This, of course, causes inconvenience to the patient, who also has to travel to the medical centers that have these devices, which, in many cases, are far from the patient's home.

Currently known methods involve injection of radioactive or contrast-enhancing substances into the bloodstream in order to observe and learn about variations in blood flow in the brain between migraine attacks and normal conditions. Examination is also possible by the invasive method of introducing probes (electrodes) directly into the brain.

Currently known measurement methods for measuring blood flow to and in the brain include Isotope Diagnosis (ID) and Transcranial Dopplerography (TCD). Isotope Diagnosis is invasive and can only be performed by intermittent sampling measurements, rather that continuous measurement in real-time.

Transcranial Dopplerography is noninvasive and does give real-time measurement, but it does not measure the volumetric velocity of the blood flow and does not give precise measurement of the contraction or dilation of blood vessels in the brain. It is therefore not useful for diagnosis of migraine. This imprecision results from the fact that TCD can only be used to observe a sector or large area in the brain, instead of a localized point. TCD uses ultrasound waves at a frequency of 2 MHz, which, for an estimated 15–40% of the population, do not actually reach the interior of the cranium, because of high attenuation of the ultrasound waves in the bone tissue of the cranium. In those cases, where there is a response from the skull or via "acoustic windows," such as the temporal bones (orbital regions or foramen occipital magna), the acoustic reflections detected are only from the magistrial and proximal blood vessels. In addition to these reflected signals, this method also detects reflections from the brain and from other, non-cranial, blood vessels. The result is a noisy signal which does not allow precise determination of the depth of the measurement point. This does not allow measurement of individual blood vessels or their blood flow with any precision. Use of ultrasound technology as a diagnostic tool is discussed, inter alia, in the book entitled "Textbook of Diagnostic Ultrasonography," $4^{th}$ edition, by Mosby, pages 682–686.

SUMMARY OF THE INVENTION

The present invention seeks to provide a method and device which facilitates observation in real-time of migraine activity. It is sought to accomplish this by detecting variations in cranial blood flow and observing the contraction or dilation of blood vessels in the brain. The technique used in the present invention is non-invasive and is based on objective measurement.

The present invention is based on ultrasound technology, with no injection of contrast-enhancing or any other substances into the bloodstream. The measurement results are displayed immediately, in real-time, on a computer display terminal, which allows immediate detection of changes in blood flow at a precisely defined location (i.e., position and depth) in blood vessels in the brain.

The time for the measurement with the present invention is negligible compared to the time required for the currently accepted methods of measurement. Measurement with the present invention is also less costly than currently accepted methods of measurement.

The present invention utilizes innovative application of ultrasound technology and the known reaction of different tissues to ultrasound waves for the diagnosis of changes in the system of blood vessels in the cranium (pathophysiology) in patients suffering from migraines. The present invention is based on analysis of reflected ultrasound pulses from the different structures in the intracranial space (i.e., brain, ventricles, vasales, and cysterns), their recording on magnetic media, and their immediate presentation, in real-time, on a computer display terminal.

There is thus provided, in accordance with a preferred embodiment of the invention, a method of real-time determination of variations in effective diameter of cranial blood vessels, thereby to provide an indication of migraine activity, which includes determining the blood flow rate to the brain of a subject; determining the intracranial blood flow rate in selected blood vessels; and comparing the intracranial blood flow rate with the determined blood flow rate to the brain thereby to determine a change in the intracranial blood flow rate relative to the blood flow rate to the brain, indicating a corresponding change in the effective diameter of the preselected blood vessel.

Additionally in accordance with a preferred embodiment of the invention, the method also includes the step, between the steps of determining the blood flow rate and determining the intracranial blood flow rate, of observing the pulsatile variations in the intracranial blood flow in selected blood vessels in real time, and further includes the step, between the steps of determining the intracranial blood flow rate and comparing, of analyzing the pulsatile variations in the intracranial blood flow in selected blood vessels thereby to determine changes in the effective diameter of the selected blood vessel.

Further in accordance with a preferred embodiment of the invention the steps of observing the pulsatile variations in the intracranial blood flow in selected blood vessels includes the sub-steps of exposing the head of the subject to pulses of ultrasound waves in a frequency waveband selected so as to not to be substantially attenuated by bone tissue, and such that the ultrasound energy is reflected; and detecting ultrasound waves reflected from the selected blood vessels;

and the step of determining intracranial blood flow rate further includes comparing reflected ultrasound waves with transmitted ultrasound waves in real-time, thereby to reveal pulsatile variations in the intracranial blood flow in selected blood vessels and to determine a rate of intracranial blood flow in the selected blood vessels.

Additionally in accordance with a preferred embodiment of the invention, the step of determining the blood flow rate to the brain includes detection of a reference pulse at a predetermined location upstream in the blood stream from the brain in synchronization with the step of observing pulsatile variations in the intracranial blood flow. Preferably, this is performed by employing ECG in synchronization with the step of determining the intracranial blood flow rate Further in accordance with a preferred embodiment of the invention the step of exposing the head of the subject to pulses of ultrasound waves includes emitting ultrasound waves in the frequency range 0.5–3.0 MHz, but preferably in the range 0.8–1.2 MHz, and having a output intensity in the range 100–300 mW/cm$^2$, but, in any case, not greater than 300 mW/cm$^2$.

In accordance with a further embodiment of the invention, there is also provided a system for performing the above method.

BRIEF DESCRIPTION OF THE DRAWINGS

The present invention will be more fully understood and appreciated from the following detailed description, taken in conjunction with the drawings, in which:

FIG. 4-A is a graphical data output display of the present embodiment of the system of the invention, obtained from a healthy subject.

FIGS. 4-B and 4-C are graphical data output displays of the present embodiment of the system of the invention, obtained from a subject suffering from migraine, for the right and left hemispheres of the brain, respectively.

DETAILED DESCRIPTION OF THE INVENTION

Figure 1:
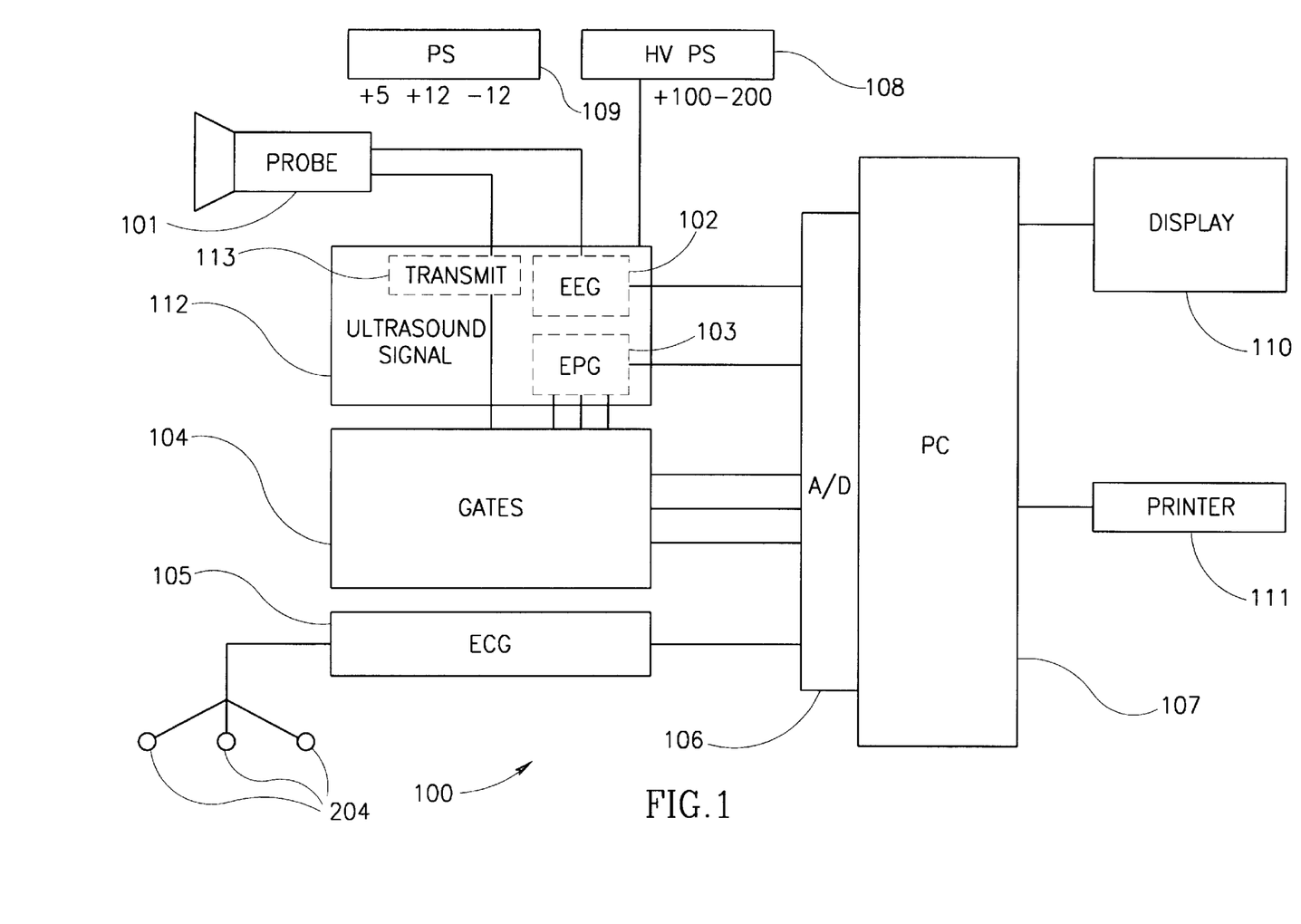
FIG. 1 is a block diagram of a system for observing variations in the blood flow in the brain, constructed and operative in accordance with an embodiment of the present invention.

Referring now to FIG. 1, the present invention provides a system, referenced generally 100, for providing an indication of the status of cranial blood vessels, dilation or contraction, as part of the chain of causes of migraine. By measuring the rate of local blood flow in real-time at a selected location in the brain and comparing it both with a) the overall rate of blood flow to the brain, and b) the rate of local blood flow at other locations in the brain, the present invention allows determination of whether there are local increases or decreases in rate of blood flow in the brain. This indicates whether selected blood vessels in the brain are dilated or contracted, which is known to be associated with migraine activity. The determination is based on the measurement of changes in the blood vessels in the brain, which indicate deviations from known normal rate of blood flow to the brain.

The changes in the rate of blood flow in the brain are measured by transmitting ultrasound waves and detecting the reflected waves. As mentioned in the Background above, prior art attempts to use Ultrasound to observe blood flow in the brain do not provide the spatial and temporal resolution of the present invention and have the additional problems of signal attenuation and noise. These factors preclude the detailed study and precise diagnosis of migraine by means of prior art.

The present invention includes a number of factors to overcome these problems. These include using ultrasound waves transmitted in pulses at a preferred frequency of 1.0±0.2 MHz, which allows use of Ultrasound power preferably of 250±50 mW/cm$^2$. The present invention includes the analysis and interpretation of the reflected pulses of ultrasound waves detected from those transmitted to the brain in a manner that provides both mean and real-time measurement of the rate of blood flow in the brain at selected locations.

Referring now to FIG. 1, it is seen that the system 100 of the present invention includes an Ultrasound probe 101, a computer 107 having an Analog to Digital (A/D) converter 106, and an Ultrasound Signal controller and processor, referenced generally 112, a Gating circuit 104, and a Electrocardiograph (ECG) 105, connected to the A/D converter 106. The system includes a suitable low-voltage power supply 109 to provide power to these circuits and a high-voltage power supply 108 to supply the Ultrasound Transmitter 113 which drives the probe 101. There are also provided a suitable display terminal 110 and printer 111, and appropriate software, as described below in conjunction with the description of computer 107. Probe 101 may be any suitable ultrasound probe for emission and detection of ultrasound waves of a frequency range of 0.5–3.0 MHz, but preferably 1.0±0.2 MHz, and having a output intensity in the range of 100–300 mW/cm2, but preferably 250±50 mW/cm2, and in any case no greater than 300 mW/cm2.

Computer 107 is provided for control of the measurement and analysis of the resulting data and may be based on any suitable microprocessor such as a 486 (or higher)-based PC. In the present embodiment of the invention, the computer 107 includes a program written to perform data collection, display, and analysis. In an alternative embodiment of the present invention, the data collection functions, which control the measurement process could be performed by a suitable dedicated microprocessor included in the Ultrasound Signal controller 112. The display and analysis program is built from two modules. A first program module displays the digital signals coming from the A/D Converter 106 which originate in the ECHO-EG 102, EPG 103, and ECG 105 circuits. A second program module allows analysis of the pulses at the specific measurement point by means of the signals from the EPG 103 and the Gating circuit 104.

These primary component circuits of the system 100 are now described in detail in conjunction with FIG. 1.

The Ultrasound Signal controller and processor 112 is responsible for generation of pulses of ultrasound waves with a frequency of 1.0±0.2 MHz, by probe 101, detection of the reflected waves or echoes, also by probe 101, and processing of the signals so detected. The reflected waves are received as one-dimensional Echo Encephalogram (ECHO-EG) 102 signals.

In the present embodiment of the invention, this Ultrasound Signal controller and processor 112 operates as follows:

The Ultrasound Transmitter 113, powered by the high-voltage power supply 108, receives a Start signal from the computer 107 via the A/D and the Gates 104. In response, it generates a series of Ultrasound pulses in the probe 101. The probe, which is typically placed at a location of interest on the head of the subject being examined, transmits the Ultrasound pulses into the head and brain of the subject and detects the Ultrasound energy reflected from various locations within the head and brain of the subject.

The reflected signal from the brain is passed by the probe 101 to the Echo Encephalogram (ECHO-EG) 102 block of the Ultrasound Signal controller and processor 112. The reflected Ultrasound pulses are received as one-dimensional digital Echo Encephalogram (ECHO-EG) 102 signals, which provides a representation of features in the head and brain of the subject along the straight line coming out of the probe 101. The ECHO-EG signal thus generated is passed to the Gating circuit and the Echo Pulsogram (EPG) block 103 of the Ultrasound Signal controller and processor 112 for further processing. The ECHO-EG signal is also passed to the A/D converter 106 in the computer 107. This is required to allow processing and presentation of the signal in digital form on the computer display 110 and for storing and recalling the data.

In the present embodiment of the invention, the Gating circuit 104 imposes a window gate on the Echo Encephalogram signal and thereby allows observation of the Ultrasound pulses reflected from a selected location in the brain in an amplified and integrated fashion. The part of the Ultrasound Signal controller and processor 112 that performs this signal processing is the Echo Pulsogram (EPG) 103 block. The EPG 103 produces a signal that represents the variation of the blood flow in the brain in real-time at the selected location. A typical resolution of the EPG circuit is 6 msec.

In the current embodiment of the invention, the Gating circuit 104, when connected to the circuits of the Ultrasound Signal controller and processor 112 and when controlled by the program in the computer 107, allows the system operator to select a location in the brain for observation and analysis.

The Electrocardiogram (ECG) 105 circuit records the pulsing of the heart muscle, in particular, the start of the pulsing, or the Systole. The present embodiment invention uses a standard ECG card, such as marketed by Aerotel™, which includes an integral power supply in the form of a nine-volt battery. In an alternative embodiment of the invention, the ECG circuit 105 receives its nine-volt supply voltage from the system power supply 109. In such a case, a protective opto-coupler (one-way electrical valve) would be included to protect the subject from this nine-volt DC voltage source.

The three analog signals produced by the present embodiment of the invention, namely, ECHO-EG, EPG, and ECG, are passed to the A/D converter 106 in the computer 107 (in the present embodiment of the invention) for transformation to digital signals for processing by the computer and for storing and recreating the signal data.

These circuits in the present embodiment of the current invention are shown in greater detail in FIGS. 3A–3F and are discussed in greater detail in relation to those figures below. The signals produced are shown as they are displayed on the display terminal 110 of the computer 107 are shown in FIGS. 4-A, 4-B, and 4-C and are discussed in relation to those figures below.

The present embodiment of the invention includes an electrical power supply 109 with an input voltage of 220 AC Volts and DC output voltages as required by the component circuits, namely, ±5 Volts and ±12 Volts and a projected embodiment of the invention includes an output of 9 Volts DC for the ECG 105. The high voltage DC power supply for the probe 101 must be a source of highly-filtered "square" DC power in the range 100–200 Volts DC.

Figure 2:
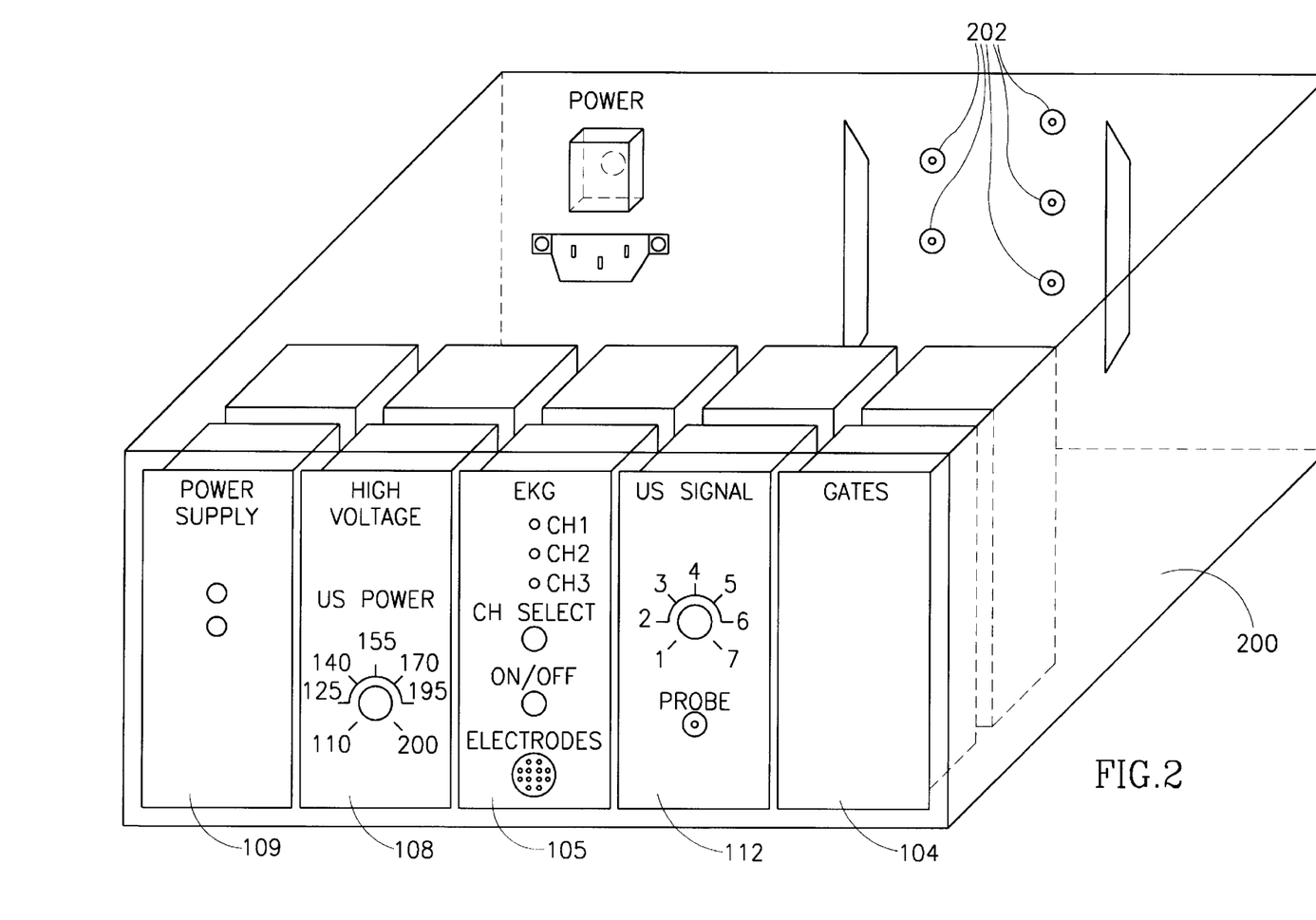
FIG. 2 is an illustration of a main unit of the system of the present invention, showing the primary components or modules of the system in their housing or cage.

FIG. 2 shows the housing or cage 200 for the primary component circuits for the present embodiment of the invention, namely the low-voltage power supply 109, the high-voltage power supply 108, the Ultrasound Signal controller and processor 112, the Gates 104, and the Electrocardiogram 105. Every slot in the cage 200 preferably has its own built-in noise-shielding circuit. On the rear panel of the cage are BNC connectors 202 for each circuit, which allow examination of the specific circuits functioning by means of an oscilloscope. This measurement allows matching up the digital signals with the analog signals.

The A/D Converter circuit 106 (FIG. 1) transforms the analog signals to digital signals. In the present embodiment of the invention, the circuit is located on a card in one of the slots of the computer 107. It could alternatively be housed in the cage 200 of the circuits described above.

Figure 3A:
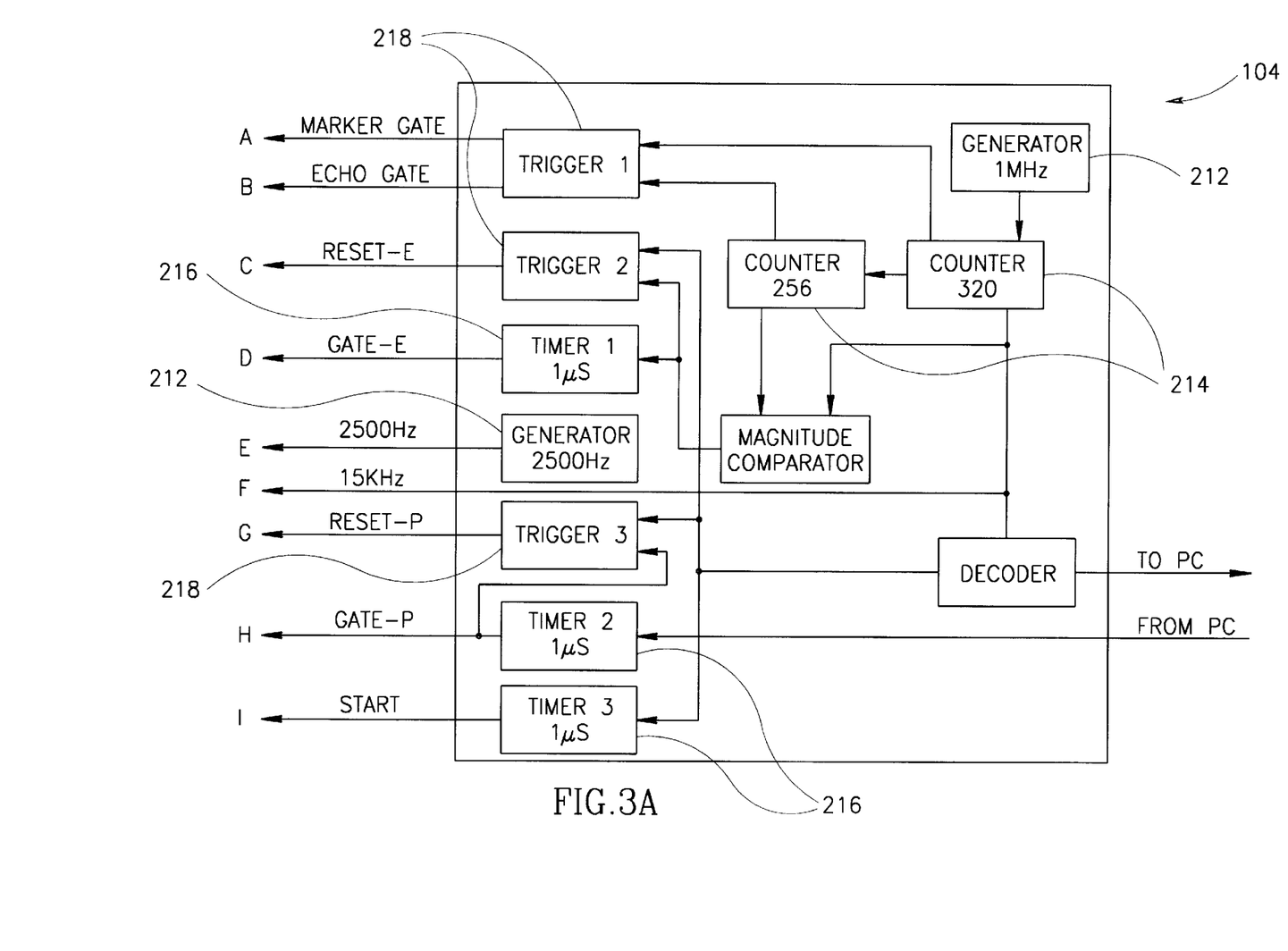
FIGS. 3A, 3B and 3C combine to form a more detailed block diagram of the modules contained in the cage in FIG. 2.
Figure 3B:
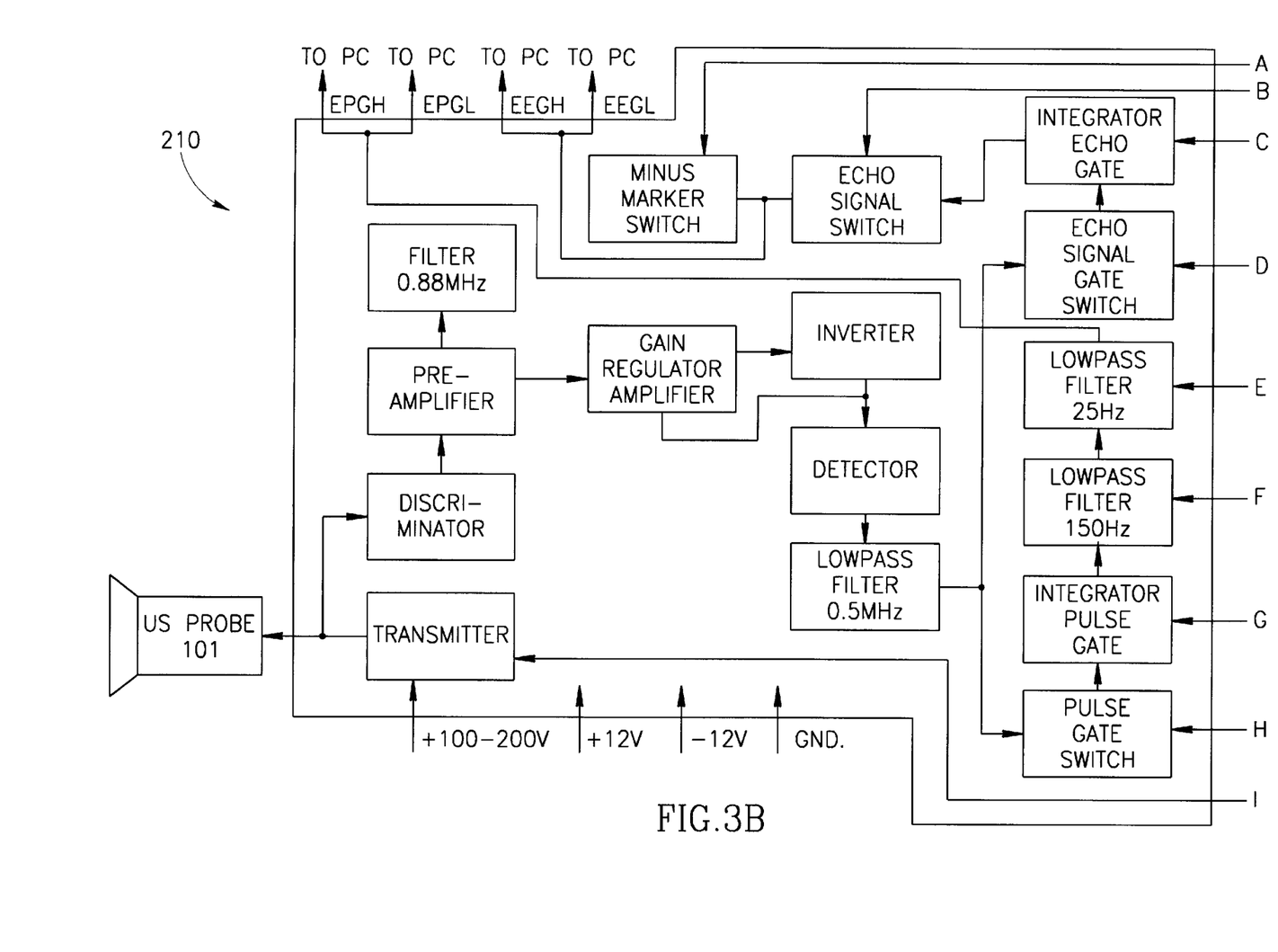
Figure 3C:
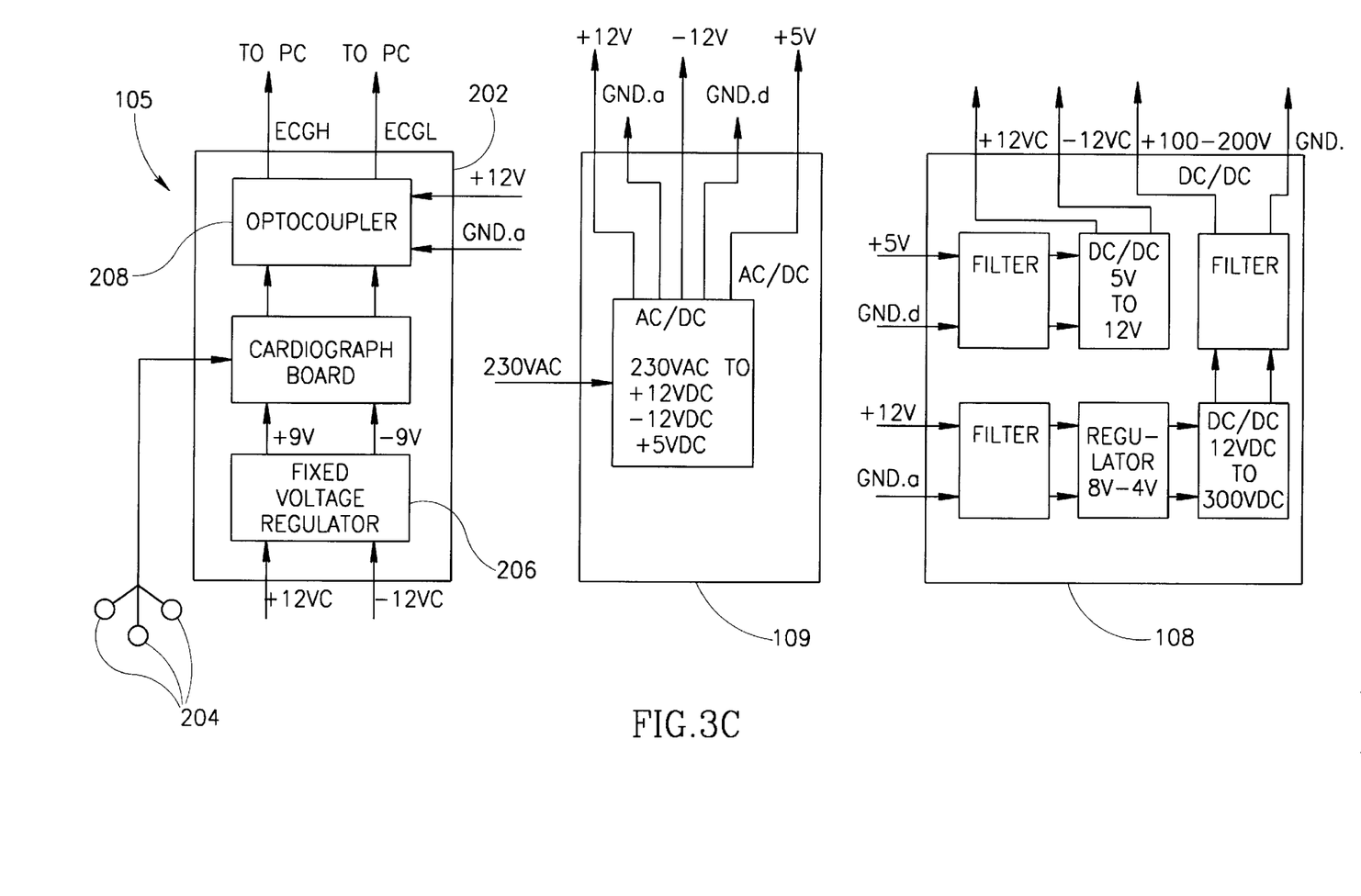
Figure 4A:
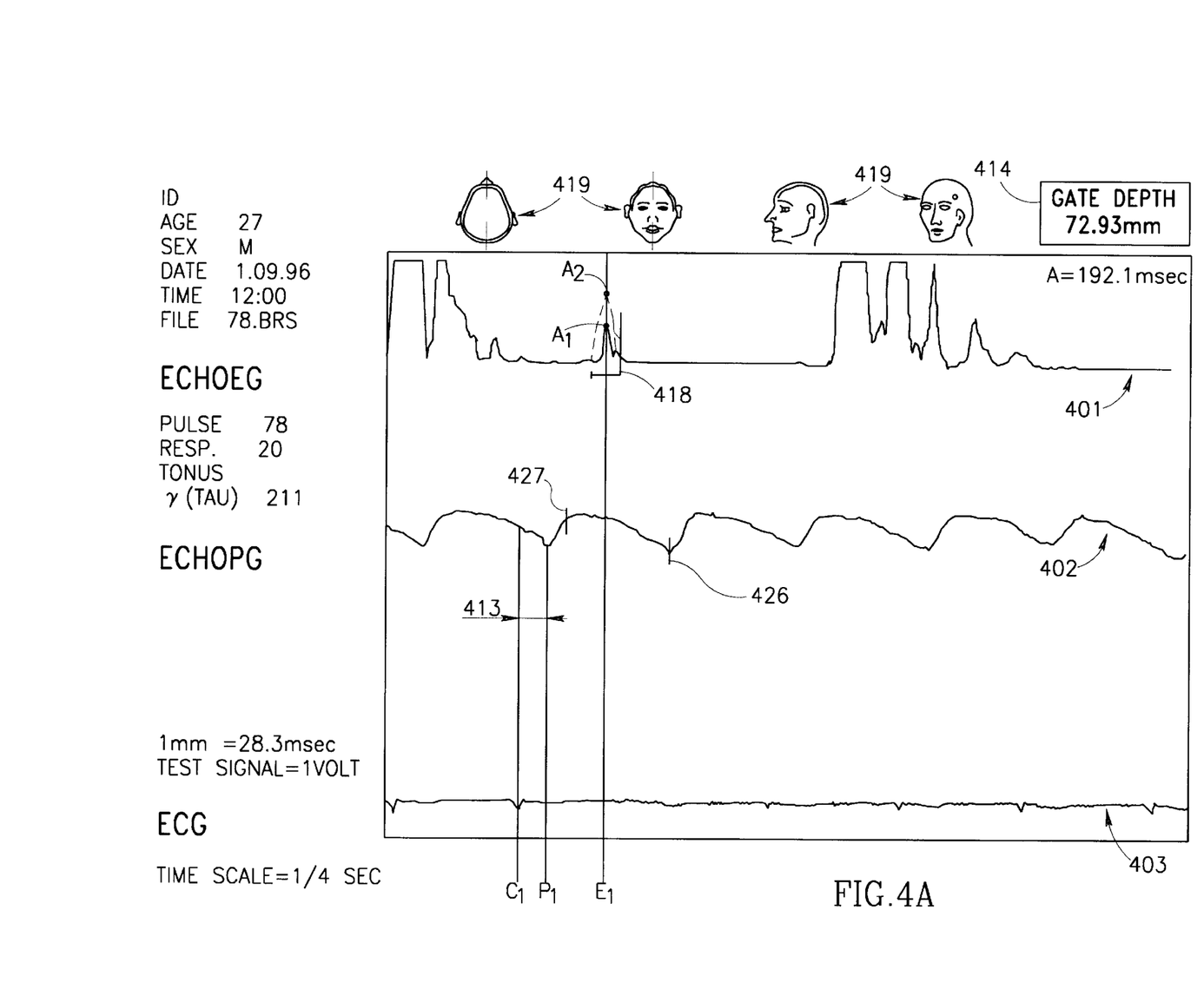
Figure 4B:
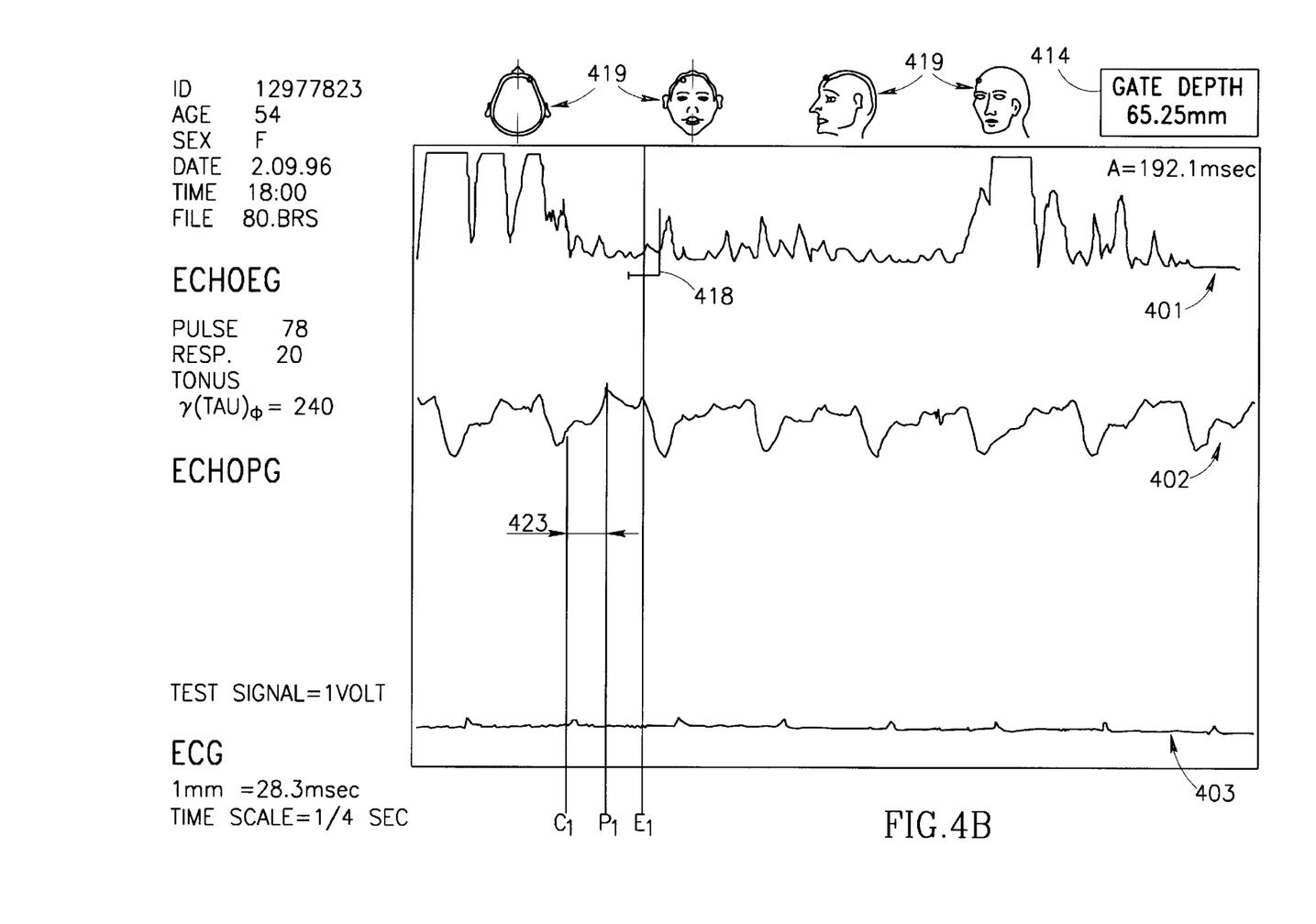
Figure 4C:
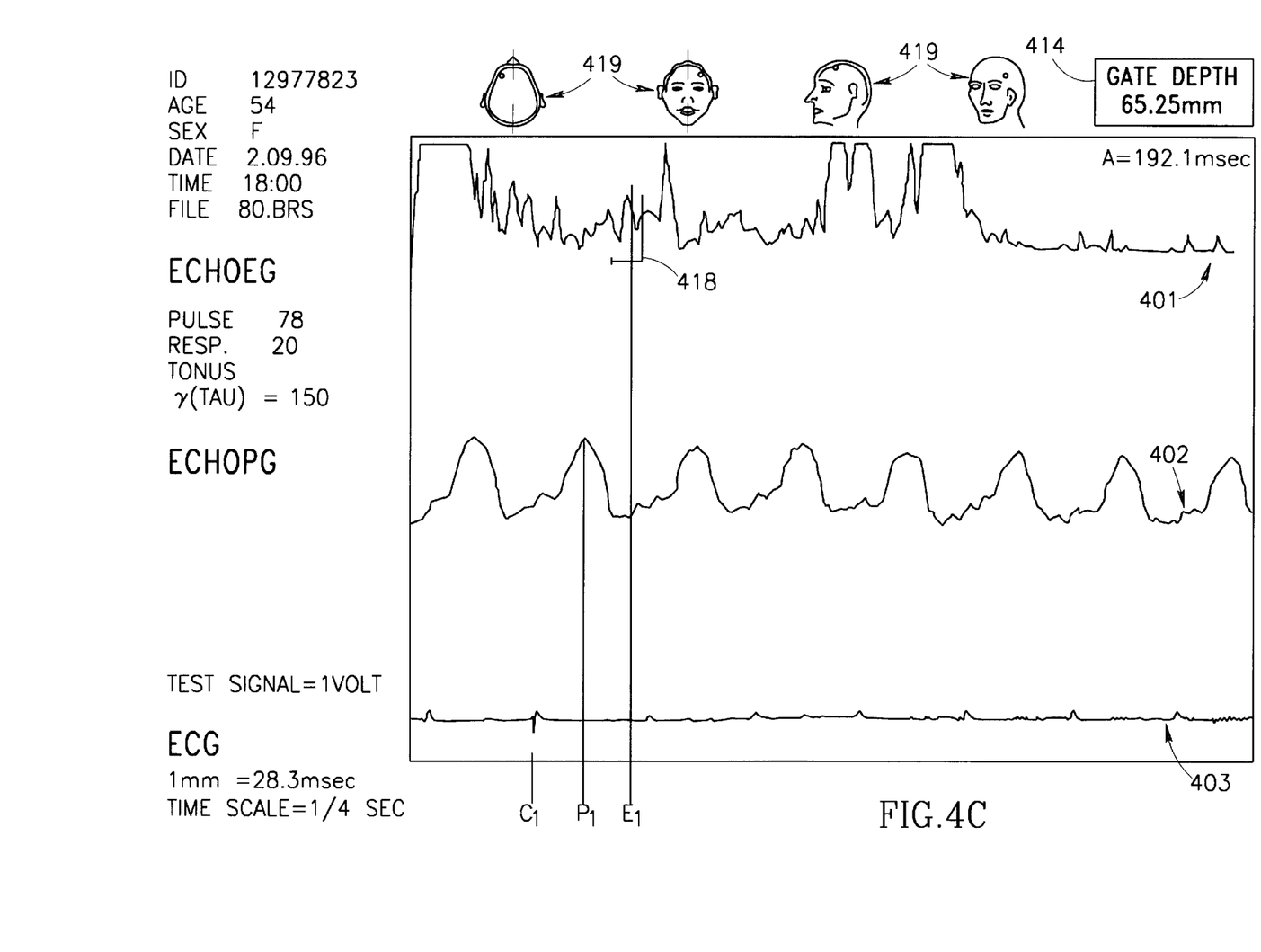

Referring now to FIGS. 3A–3C, the major circuit blocks in FIG. 1 are seen in more detail.

With particular reference to FIG. 3C, the ECG or Electrocardiograph circuit block 105, which is included in the present embodiment of the invention, is built around an Aerotel™ model 400 Electrocardiograph circuit board 202 which is connected to the ECG electrodes 204 placed on the subject. This is supported by a voltage regulator circuit 206 to supply its required operating voltage. The ECG can be powered either by the DC power of the circuit cage 200 or by a battery. In an embodiment where the ECG power is supplied by the DC power of the circuit cage, a protective Optocoupler or one-way electrical valve circuit 208 can be included to protect the subject from the voltage source.

It is important to note the ECG signal in the present embodiment of the invention provides a reference event at a selected location upstream in the bloodstream. This establishes a reference starting time for blood flowing to the brain, which can be used to determine the rate of blood flow to the brain. The contraction of the heart muscle (Systola) detected by the ECG 105, which can be seen in the ECG signal in the example of the graphical data output display of the current system in FIG. 4-A, serves as this reference starting time. The present invention includes alternative embodiments which use any other suitably precise method of determining a reference starting time for measuring the rate of blood flow to the brain. For example, the pulse in the carotid artery, which supplies blood to the brain, could also be detected by either electrostatic (ECG) or acoustic means to serve as the required reference starting time.

The Ultrasound Signal processing circuit block 210 (FIG. 3B) is discussed in detail below with respect to FIGS. 3A–3C.

With particular reference to FIG. 3A, the Gates circuit block 104 uses methods of signal processing familiar to those versed in the art. It includes Frequency Generator circuits 212, Counter circuits 214, Timer circuits 216, and Trigger circuits 218. It chooses a segment of the actual ECHO-EG signal for integration in time to produce the EPG signal. It also includes the circuitry to display the gate on the displayed ECHO-EG signal, shown in FIG. 4-A, for example, so the operator can select a particular portion of the ECHO-EG display for EPG analysis.

FIG. 3C includes two Power Supply circuit blocks 108 and 109. The low voltage power supply 109 may be any suitable conventional power supply. The high voltage (100–200 Volts DC) supply 108 is preferably a source of highly-filtered "square" DC power, which is required for the reduction of noise in the system.

Figure 3D:
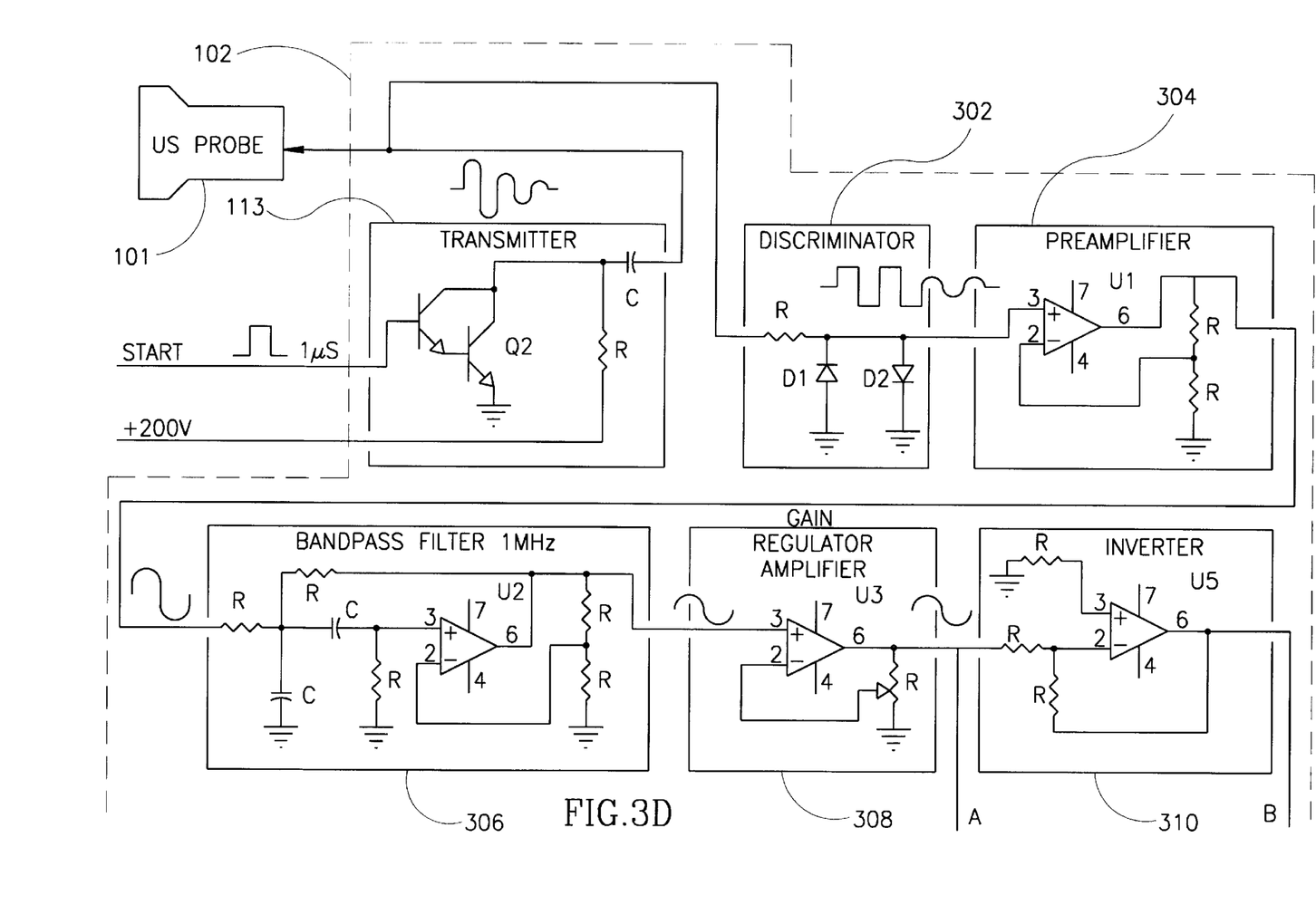
FIGS. 3D, 3E and 3F combine to form a more detailed block diagram of the circuits performing the primary ultrasound signal processing functions, the Echo Encephalogram (ECHO-EG) and the Echo PulsoGram (EPG).
Figure 3E:
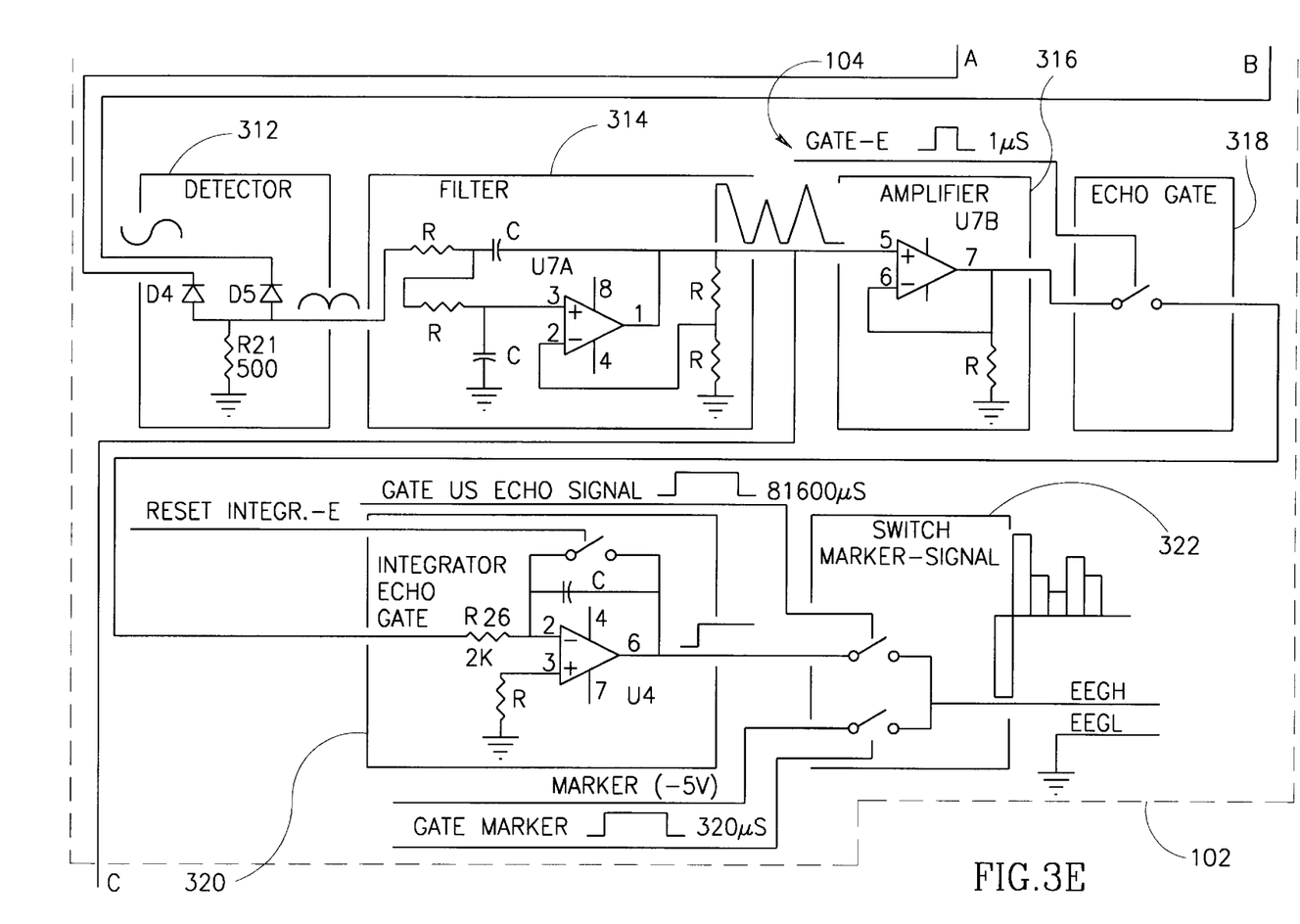
Figure 3F:
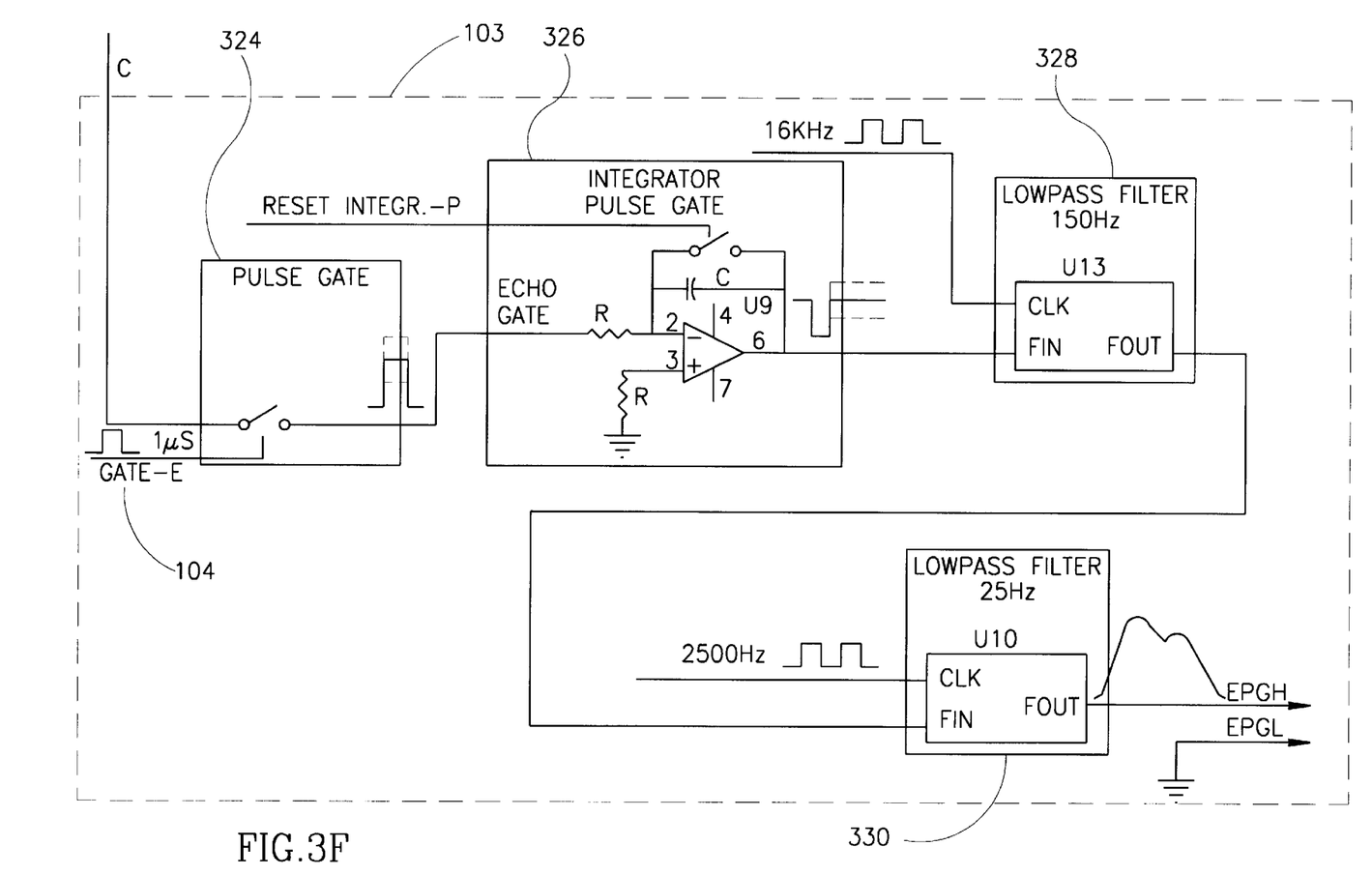

Referring now to FIGS. 3D–3F, the breakdown of the primary Ultrasound Signal processing functions, the Echo Encephalogram (ECHO-EG) 102 and the Echo Pulsogram (EPG) 103 is shown.

With particular reference to FIG. 3D, the probe 101 receives the driving ultrasound frequency (1.0±0.2 MHz) signal from the Transmitter circuit 113, which is controlled by a Start signal received from the computer 107 via the A/D Converter 106 (FIG. 1). The probe 101 also detects the reflected Ultrasound signal which is processed by the Discriminator 302, Preamplifier 304, Bandpass Filter 306, and Gain Regulator Amplifier circuits 308 in the ECHO-EG block, referenced 102, of the Ultrasound Signal Processor 112. The processed signal is modified by an Inverter 310 and a dual-diode Detector circuit 312 (FIG. 3E) and processed by a Filter circuit 314 (FIG. 3E) to produce the ECHO-EG signal for analysis and display.

With particular reference to FIG. 3D, the ECHO-EG signal is then amplified by an Amplifier circuit 316 and then the Gate 104 for the display (See description of FIG. 4-A below) is added by an Echo Gate Switch circuit 318, Echo Gate Integrator circuit 320, and Marker Signal Switch circuit 322. With particular reference to FIG. 3D, the unamplified ECHO-EG signal is also routed to the circuits of the EPG 103, which, based on the signal from the Gate circuit 104 process a portion of the ECHO-EG curve to produce the EPG curve. The EPG includes a Pulse Gate circuit 324, the Pulse Gate Integrator circuit 326, and a pair of Lowpass Filter circuits 328 and 330 which produce the EPG signal for analysis and display. They are preferably arranged as shown in FIG. 3F.

The significance of two signals, ECHO-EG and EPG, together with the Gate 104 are explained below with respect to FIG. 4-A, which is an example of a the graphical data output display produced by the present embodiment of the invention. These signals are digitized by an A/D Converter 106 circuit for storage, analysis, and display by the computer 107.

As was pointed out above, with respect to FIG. 2, the A/D Converter circuit 106, which transforms the analog signals to digital signals, is located, in the present embodiment of the invention, on a card in one of the slots of the computer 107. It could also be housed in the cage 200 of the special circuits described above.

FIGS. 4-A, 4-B, and 4-C are printouts of examples of graphical data output display obtained with the present embodiment of a system according to this invention as displayed on the display terminal of the computer 107. The displays each include three signals: the Echo Encephalogram (ECHO-EG) signal, the Echo Pulsogram (EPG) signal, and the Electrocardiograph (ECG) signal, which are described below. FIG. 4-A represents data obtained from a healthy subject. FIGS. 4-B and 4-C represent data obtained from a subject diagnosed independently to be suffering from migraine, for the right and left hemispheres of the brain, respectively.

The three signals graphically represented in each figure are used by the present invention to characterize the blood flow in the brain. The signals, as shown in FIG. 4-A, are as follows:

The Echo Encephalogram (ECHO-EG) signal 401 graphically shows modulation in the reflected ultrasound waves detected when ultrasound waves are transmitted through the cranium to blood vessels in the brain. The modulation is a function of time from the transmission of the signal and bears a one-to-one relationship with the depth of the point of reflection. This means the ECHO-EG signal 401 is a representation of features in the head and brain of the subject along the straight line coming out of the probe 101 (FIG. 1). The gate 418 superimposed on the ECHO-EG signal indicates the specific portion of the curve being observed in the Echo Pulsogram (EPG) signal, which corresponds to the location in the brain selected for observation.

The Echo Pulsogram (EPG) signal 402 graphically shows modulation of the total (integrated) detected ultrasound signal from the area selected by the gate on the ECHO-EG signal 401 as a function of time. This signal 402 provides a measure in real-time of the condition of the blood vessels (contraction or dilation) represented by the selected area in the ECHO-EG signal 401. The EPG signal 402 is displayed in the same units of amplitude as the ECHO-EG signal 401.

The Electrocardiograph (ECG) signal 403 presents graphically modulation of the signal from the heart muscle as a function of time. This signal shows the start (Systola) and other details of each heartbeat in real-time.

The time units of the horizontal axes are the same for the EPG signal 402 and ECG signal 403, but not for the ECHO-EG signal 401.

Descriptions of additional details shown on the data output display are as follows:

In FIG. 4-A, Point C1 on the graph of the ECG signal 403 is the starting time of the Systola of the heart. Point P1 on the graph of the EPG signal 402 is the starting time for the pulse in the selected blood vessel in the brain.

The time interval 413 between points C1 and P1 represents the time for blood to flow from the heart to the brain, which is also the delay between the ECG and Echo-PG signals. This interval is called tau ($\tau$). In the example pictured in FIG. 4-A, the time $\tau$ is 211 msec.

The depth of the measurement point is displayed in the box 414 labeled "Gate Depth" in the upper right of the graph 414. This point corresponds to the point in the ECHO-EG signal graph selected by the gate 418. In this case, the Gate Depth is 72.93 mm. This point is labeled on the graph as point E1.

Looking at that part of the graph of the ECHO-EG signal 401 enclosed by the gate 418, there are two peaks A1 and A2 shown at the same point, referenced E1, in the signal graph. The peaks A1 and A2 represent a blood vessel in the brain in the respective states of Diastole and Systole. Looking now at the graph of the EPG signal 402, which is the reflected Ultrasound signal in the area enclosed by the gate 418 as a function of time, these two points are the respective minimum and maximum points, 426 and 427, of the EPG signal 402. The rise time and fall time of this signal represents the rise time and fall time of the pulse in the blood vessel in the brain. The shape of the EPG waveform 402 indicates the status of the blood vessel and can be used to deduce the presence of migraine activity. This representation is the usual one for this type of graph.

For the typical, healthy, population, the time for blood to flow from the heart to the brain is 211±6 msec.

Note also that the examination point on the skull is indicated on the pictographs 419 above the graph.

In FIG. 4-B, the data is for a subject suffering from migraine, right side of brain. The time interval 423 between points C1 and P1 is 240 msec at a depth of 65.25 mm. This reading indicates a contraction of the blood vessels in this part of the brain, since the time for blood to flow to the brain is longer than average.

In FIG. 4-C, the data is for a the same subject suffering from migraine, left side of brain. The time interval 433 between points C1 431 and P1 432 is 150 msec at a depth of 65.25. This reading indicates a dilation of the blood vessels in this part of the brain, since the time for blood to flow to the brain is shorter than average.

As indicated above, the normal time for blood to flow from the heart to the brain is 211±6 msec.

The significance of the data presented in the EPG signal graphs in FIGS. 4-B and 4-C is that there is an asymmetry in the speed of the blood flow to the two hemispheres of the brain. Very often the dilation of the blood vessels in one hemisphere of the brain is a result of compensation by that part of the brain in reaction to contraction of the blood vessels in the other hemisphere of the brain. This asymmetry is indicative of migraine.

It will be appreciated by persons skilled in the art, that the scope of the present invention is not limited by what has been specifically shown and described hereinabove, merely by way of example. Rather, the scope of the present invention is defined solely by the claims, which follow.

I claim:

1. A method of real-time determination of variations in effective diameter of cranial blood vessels, thereby to provide an indication of migraine activity, which comprises:

determining the blood flow rate to the brain of a subject;

determining the intracranial blood flow rate in selected blood vessels; and comparing said intracranial blood flow rate with said determined blood flow rate to the brain thereby to determine a change in said intracranial blood flow rate relative to said blood flow rate to the brain, indicating a corresponding change in the effective diameter of the preselected blood vessel.

2. A method according to claim 1, and also comprising the step, between said steps of determining the blood flow rate and determining the intracranial blood flow rate, of observing the pulsatile variations in the intracranial blood flow in selected blood vessels in real time, and further comprising the step, between said steps of determining the intracranial blood flow rate and comparing, of analyzing said pulsatile variations in the intracranial blood flow in selected blood vessels thereby to determine changes in the effective diameter of the selected blood vessel.

3. A method according to claim 2, wherein said steps of observing the pulsatile variations in the intracranial blood flow in selected blood vessels comprises the following sub-steps:

exposing the head of the subject to pulses of ultrasound waves in a frequency waveband selected so as to not to be substantially attenuated by bone tissue, and such that the ultrasound energy is reflected;

detecting ultrasound waves reflected from said selected blood vessels; and said step of determining intracranial blood flow rate further comprises comparing reflected ultrasound waves with transmitted ultrasound waves in real-time, thereby to reveal pulsatile variations in the intracranial blood flow in selected blood vessels and to determine a rate of intracranial blood flow in the selected blood vessels.

4. A method according to claim 2, and wherein said step of determining the blood flow rate to the brain comprises detection of a reference pulse at a predetermined location upstream in the blood stream from the brain in synchronization with said step of observing pulsatile variations in the intracranial blood flow.

5. A method according to claim 4, wherein said step of detection of a reference pulse at a predetermined location in the blood stream outside the brain includes the sub-step of employing ECG in synchronization with said step of determining the intracranial blood flow rate.

6. A method according to claim 3, wherein said step of exposing the head of the subject to pulses of ultrasound waves comprises emitting ultrasound waves in the frequency range 0.5–3.0 MHz, and having a output intensity in the range 100–300 mW/cm$^2$.

7. A method according to claim 3, wherein said step of exposing the head of the subject to pulses of ultrasound waves comprises emitting ultrasound waves in the frequency range 0.8–1.2 MHz.

8. A method according to claim 3, wherein said step of exposing the head of the subject to pulses of ultrasound waves comprises emitting ultrasound waves having an output intensity in the range 200–300 mW/cm$^2$.

9. A method according to claim 3, wherein said step of exposing the head of the subject to pulses of ultrasound waves, comprises emitting ultrasound waves having a output intensity not greater than 300 mW/cm$^2$.

10. A system for real-time determination of variations in effective diameter of cranial blood vessels, thereby to provide an indication of migraine activity, which comprises:

means for determining the blood flow rate to the brain of a subject;

means for determining the intracranial blood flow rate in selected blood vessels; and means for comparing said intracranial blood flow rate with said determined blood flow rate to the brain thereby to determine a change in said intracranial blood flow rate relative to said blood flow rate to the brain, indicating a corresponding change in the effective diameter of the preselected blood vessel.

11. A system according to claim 10, and also comprising means for observing the pulsatile variations in the intracranial blood flow in selected blood vessels in real time, and means for analyzing said pulsatile variations in the intracranial blood flow in selected blood vessels thereby to determine changes in the effective diameter of the selected blood vessel.

12. A system according to claim 11, wherein means for observing the pulsatile variations in the intracranial blood flow in selected blood vessels comprises:

means for transmitting to the head of the subject pulses of ultrasound waves in a frequency waveband selected so as to not to be substantially attenuated by bone tissue and so as to be reflected from the selected blood vessels, and means for detecting reflected ultrasound energy; and said means for determining intracranial blood flow rate further comprises means for comparing reflected ultrasound waves with transmitted ultrasound waves in real-time, thereby to reveal pulsatile variations in the intracranial blood flow in selected blood vessels and to determine a rate of intracranial blood flow in the selected blood vessels.

13. A system according to claim 11, and wherein said means for determining the blood flow rate to the brain comprises means for detecting a reference pulse at a predetermined location upstream in the blood stream from the brain together with operation of said means for observing pulsatile variations in the intracranial blood flow.

14. A system according to claim 13, wherein said means for detecting comprises electrocardiogram means.

15. A system according to claim 12, wherein said means for transmitting ultrasound waves comprises means for transmitting ultrasound waves in the frequency range 0.5–3.0 MHz, and at an output intensity in the range 100–300 mW/cm$^2$.

16. A system according to claim 12, wherein said means for transmitting ultrasound waves comprises means for transmitting ultrasound waves in the frequency range 0.8–1.2 MHz.

17. A system according to claim 12, wherein said means for transmitting ultrasound waves comprises means for transmitting ultrasound waves having an output intensity in the range 200–300 mW/cm$^2$.

18. A system according to claim 12, wherein said means for transmitting ultrasound waves comprises means for transmitting ultrasound waves having a output intensity not greater than 300 mW/cm$^2$.

* * * * *